US00PP28109P3

(12) United States Plant Patent
Ubink

(10) Patent No.: US PP28,109 P3
(45) Date of Patent: Jun. 13, 2017

(54) ***PACHYPHYTUM* PLANT NAMED 'DRACO'**

(50) Latin Name: *Pachyphytum hybrida*
Varietal Denomination: Draco

(71) Applicant: Gert Ubink, Kudelstaart (NL)

(72) Inventor: Gert Ubink, Kudelstaart (NL)

(73) Assignee: Handelskwekerij UBink B.V., Kudelstaart (NL)

( * ) Notice: Subject to any disclaimer, the term of this patent is extended or adjusted under 35 U.S.C. 154(b) by 99 days.

(21) Appl. No.: 14/756,355

(22) Filed: Sep. 1, 2015

(65) Prior Publication Data

US 2017/0064897 P1 Mar. 2, 2017

(51) Int. Cl.
*A01H 5/00* (2006.01)

(52) U.S. Cl.
USPC ..... Plt./373

(58) Field of Classification Search
USPC ..... Plt./373, 372
CPC ..... A01H 5/00
See application file for complete search history.

*Primary Examiner* — Kent L Bell

(57) ABSTRACT

A new cultivar of *Pachyphytum* plant named 'Draco' that is characterized by oblanceolate shaped leaves that curve upward, leaves that are resistant to dropping and grey-green leaves suffused with purple toward the margins.

1 Drawing Sheet

Botanical classification: *Pachyphytum hybrida.*
Variety denomination: 'Draco'.

BACKGROUND OF THE INVENTION

The present invention relates to a new and distinct cultivar of *Pachyphytum* plant botanically known as *Pachyphytum hybrida* and hereinafter referred to by the cultivar name 'Draco'.

'Draco' originated from the crossing of the female or seed parent an unnamed proprietary *Pachyphytum bracteosum* cultivar and the male or pollen parent an unnamed proprietary *Pachyphytum hookeri* cultivar. The crossing was conducted in 2009 in Kudelstaart, Netherlands. The resulting seeds were subsequently planted and grown. The cultivar 'Draco' was selected by the inventor in 2010 in a controlled environment as a single plant within the progeny of the stated cross in a cultivated area of Kudelstaart, Netherlands.

Asexual reproduction of the new cultivar 'Draco' first occurred by leaf cuttings in 2010 in Kudelstaart, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Pachyphytum* cultivar 'Draco'. These traits in combination distinguish 'Draco' as a new and distinct cultivar apart from other existing varieties of *Pachyphytum* known by the inventor.

1. *Pachyphytum* 'Draco' exhibits oblanceolate shaped leaves that curve upward.
2. *Pachyphytum* 'Draco' exhibits leaves that are resistant to dropping.
3. *Pachyphytum* 'Draco' exhibits grey-green leaves suffused with purple toward the margins.

The closest comparison cultivars are *Echeveria* 'Lila Cina' (not patented) and the co-pending application cultivar *Pachyphytum* 'Corvus' (U.S. Plant patent application No. 14/756,347).

'Draco' is distinguishable from 'Lila Cina' by the following characteristics:

1. *Pachyphytum* 'Draco' exhibits narrower leaves than the leaves of 'Lila Cina'.
2. *Pachyphytum* 'Draco' exhibits leaves that curve upward more than the leaves of 'Lila Cina'.
3. *Pachyphytum* 'Draco' exhibits grey-green leaves suffused with purple toward the margins. The leaves of 'Lila Cina' are grey.

'Draco' is distinguishable from 'Corvus' by the following characteristics:

1. *Pachyphytum* 'Draco' exhibits longer leaves than the leaves of 'Corvus'.
2. *Pachyphytum* 'Draco' exhibits grey-green leaves suffused with purple toward the margins. The leaves of 'Corvus' are blue-green.

'Draco' is distinguishable from the female parent plant, an unnamed proprietary *Pachyphytum bracteosum* cultivar, by the following characteristics:

1. *Pachyphytum* 'Draco' exhibits a larger overall size than the female parent plant.
2. The leaves of 'Draco' are more firmly attached to the plant. The leaves of the female parent plant frequently drop off 'Draco' is distinguishable from the male parent plant parent plant, an unnamed proprietary *Pachyphytum hookeri* cultivar, by the following characteristics:

1. The leaves of 'Draco' are wider than the leaves of the male parent plant.
2. The leaves of 'Draco' are flatter than the leaves of the male parent plant.

BRIEF DESCRIPTION OF THE DRAWING

The accompanying photograph illustrates the distinguishing traits of *Pachyphytum* 'Draco'. The photograph shows an overall view of a 12 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Pachyphytum* cultivar named 'Draco'. Data was collected in Kudelstaart, Netherlands from 12 month old plants grown in a glass greenhouse in 10.5 cm. diameter containers. The time of year was April and the temperature range was 18-20 degrees Centigrade during the day and 14-16 degrees Centigrade at night. The light level was natural light level. No photoperiodic treatments or growth retardants were used. Color determinations are in accordance with The Royal Horticultural Society Colour Chart 2007 edition, except where general color terms of ordinary dictionary significance are used. The growing requirements are similar to the species. 'Draco' has not been tested under all possible conditions and phenotypic differences may be observed with variations in environmental, climatic, and cultural conditions, however, without any variance in genotype.

Botanical classification: *Pachyphytum hybrida* 'Draco'.

Annual or perennial: Perennial.

Parentage: 'Draco' is a hybrid of the female parent an unnamed proprietary *Pachyphytum bracteosum* cultivar and the male or pollen parent an unnamed proprietary *Pachyphytum hookeri* cultivar.

Plant type: Pot plant.

Plant shape: Basal rosette.

Suitable container size: 7 cm. pots or larger.

Plant height: 8.9 cm.

Plant width: 12.5 cm.

Vigor: Moderate.

Low temperature tolerance: 10° Centigrade.

High temperature tolerance: 40° Centigrade.

Propagation: Leaf cuttings.

Time to initiate roots (summer): 14 days at 20° C.

Time to initiate roots (winter): 21 days at 20° C.

Time to produce a rooted cutting (summer): 120 days at 20° C.

Time to produce a rooted cutting (winter): 150 days at 20° C.

Growth rate: Leaves grown approximately 0.5 cm. per month.

Crop time: Approximately 12 months in Kudelstaart, Netherlands.

Root system: Fibrous.

Root color: N155.

Plant fragrance: None.

Foliage:

*Leaf arrangement.*—Basal rosette.

*Compound or single.*—Single.

*Quantity of leaves per plant.*—Average 37.

*Leaf shape.*—Oblanceolate, moderately concave, slightly carinate.

*Leaf apex.*—Broad short apiculate.

*Leaf base.*—Broad cuneate.

*Leaf dimensions.*—6.3 cm. in length and 2.5 cm. in width.

*Leaf thickness.*—0.9 cm.

*Texture.*—Glabrous both surfaces, succulent.

*Pubescence.*—Absent.

*Leaf margin.*—Entire.

*Venation pattern.*—None visible.

*Young leaf color* (*upper surface*).—191A, suffused with N77C toward margins, base 145D, covered by waxy layer 188B.

*Young leaf color* (*lower surface*).—Between 191A and 194A, suffused with N77C toward margins, base 145D, covered by waxy layer 188B.

*Mature leaf color* (*upper surface*).—189A, covered by waxy layer 188B.

*Mature leaf color* (*lower surface*).—Between 148B and 189A, covered by waxy layer 188B.

*Durability of foliage to stress.*—High.

*Leaf attachment.*—Sessile.

Flower: No flowers have been observed to date.

Fruit and seed: Fruit or seed production has been observed to date.

Disease and pest resistance: Disease and pest resistance has not been observed.

The invention claimed is:

1. A new and distinct variety of *Pachyphytum* plant named 'Draco' as described and illustrated.

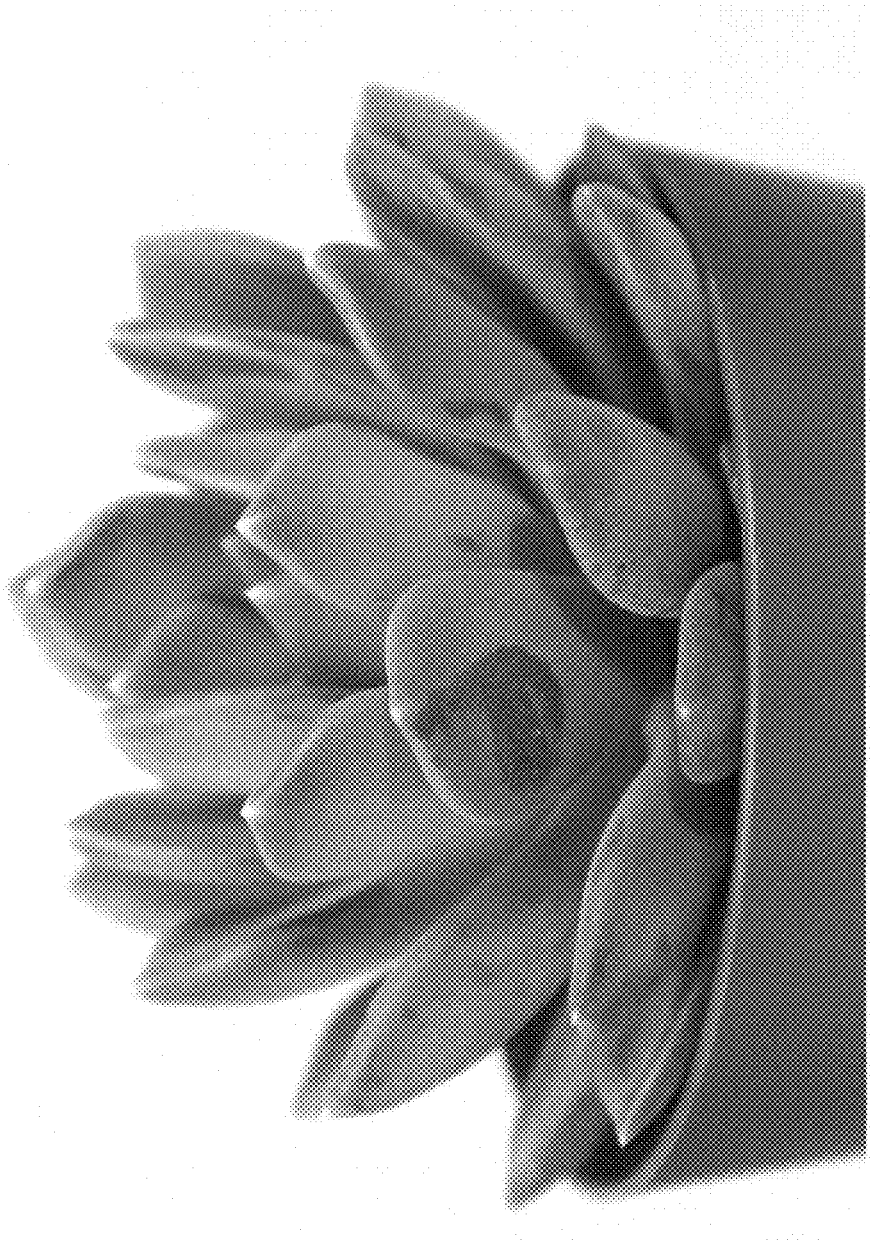

* * * * *